United States Patent

Sarria Toro et al.

(10) Patent No.: US 9,663,420 B2
(45) Date of Patent: May 30, 2017

(54) CYCLOPROPANATION

(71) Applicant: ETH Zurich, Zurich (CH)

(72) Inventors: Juan Manuel Sarria Toro, Zürich (CH); Peter Chen, Zollikerberg (CH); Tim Den Hartog, Zürich (CH)

(73) Assignee: ETH Zurich, Zurich (CH)

( * ) Notice: Subject to any disclaimer, the term of this patent is extended or adjusted under 35 U.S.C. 154(b) by 0 days.

(21) Appl. No.: 15/034,760

(22) PCT Filed: Nov. 6, 2014

(86) PCT No.: PCT/EP2014/073932
§ 371 (c)(1),
(2) Date: May 5, 2016

(87) PCT Pub. No.: WO2015/067696
PCT Pub. Date: May 14, 2015

(65) Prior Publication Data
US 2016/0280617 A1    Sep. 29, 2016

(30) Foreign Application Priority Data

Nov. 7, 2013    (GB) .................................. 1319677.9

(51) Int. Cl.
*C07C 2/86*    (2006.01)

(52) U.S. Cl.
CPC ............ *C07C 2/86* (2013.01); *C07C 2101/02* (2013.01); *C07C 2102/02* (2013.01); *C07C 2102/24* (2013.01); *C07C 2103/62* (2013.01); *C07C 2103/66* (2013.01); *C07C 2531/22* (2013.01); *C07C 2531/24* (2013.01)

(58) Field of Classification Search
CPC  C07C 2/86; C07C 13/04; C07C 13/45; C07C 13/605; C07C 2101/02; C07C 2102/02; C07C 2102/24; C07C 2103/62; C07C 2103/66; C07C 2531/22; C07C 2531/24
See application file for complete search history.

(56) References Cited

U.S. PATENT DOCUMENTS

| | | | |
|---|---|---|---|
| 3,167,594 A * | 1/1965 | Koster ..................... | C07C 1/321 568/6 |
| 8,497,384 B2 | 7/2013 | Thathagar et al. | |
| 2011/0301359 A1 | 12/2011 | Thathagar et al. | |

FOREIGN PATENT DOCUMENTS

| WO | WO 02/04398 A1 | 1/2002 |
|---|---|---|
| WO | WO 2010/055106 A1 | 5/2010 |

OTHER PUBLICATIONS

PCT/EP2014/073932—International Search Report, mailed Jan. 21, 2015.
PCT/EP2014/073932—International Written Opinion, mailed Jan. 21, 2015.
GB1319677.9—Great Britain Search Report, mailed May 13, 2014.
Den Hartog, et al., "A Palladium-Catalyzed Methylenation of Olefins Using Halomethylboronate Reagents", Organic Letters, Feb. 3, 2014, pp. 1100-1103, vol. 16, Issue 4.
Herrmann, et al., "Palladacycles as Structurally Defined Catalysts for the Heck Oldefination of Chloro- and Bromoarenes", Angewandte Chemie International, Sep. 15, 1995, pp. 1844-1848, vol. 34, Issue 17. Abstract only.
Molander, et al, "Synthesis of Amido-methyltrifluoroborates and Their Use in Cross-Coupling Reactions", Organic Letters, Sep. 29, 2010, pp. 4876-4879, vol. 12, Issue 21.
Molander, et al., "Potassium Boc-Protected Secondary Aminomethyltrifluoroborates: Synthesis and Suzuki-Miyaura Cross-Coupling Reactions", Organic Letters, Aug. 29, 2012, pp. 4458-4461, vol. 14, Issue 17.
Zapf, et al., "Fine Chemical Synthesis with Homogeneous Palladium Catalysts: Examples, Status and Trends", Topics in Catalysis, Mar. 2002, pp. 101-109, vol. 19, Issue 1. Abstract Only.

* cited by examiner

*Primary Examiner* — Sharon Pregler
(74) *Attorney, Agent, or Firm* — Curatolo Sidoti Co., LPA; Joseph G. Curatolo; Salvatore A. Sidoti

(57) ABSTRACT

A method of preparing a cyclopropane ring-bearing compound of the formula I

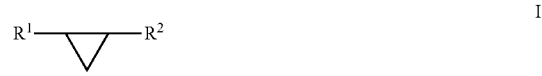

in which $R^1$ and $R^2$ are independently selected from $C_1$-$C_{10}$ alkyl, optionally substituted, or $R^1$ and $R^2$, together with the bonds linking them to the cyclopropane ring, form a monocyclic or bicyclic ring system, which may comprise at least one hetero-atom, comprising the reaction of a compound of formula II $$R^1\text{—CH}=\text{CH—}R^2 \qquad \text{II}$$

in which $R^1$ and $R^2$ have the significances hereinabove defined, with a compound of formula III $$X\text{—CH}_2\text{—Y} \qquad \text{III}$$

in which X is a nucleofuge selected from halides and pseudohalides and Y is an electrofuge selected from boranes and borates, in the presence of a metal catalyst complex selected from those useful for catalytic cyclopropanation and those useful for catalyzing Heck coupling. The method provides a particularly easy and non-hazardous method of cyclopropanation.

4 Claims, No Drawings

CYCLOPROPANATION

CROSS REFERENCE TO RELATED APPLICATIONS

This application is a national stage application of International Application No. PCT/EP2014/073932, filed 6 Nov. 2014, which claims priority from Great Britain Patent Application No. 1319677.9, filed 7 Nov. 2013, which applications are incorporated herein by reference.

The work leading to this invention has received funding from the European Union Seventh Framework Programme (FP7/2007-2013) under grant agreement No. PIEF-GA-2010-275400. and the Swiss National Science Foundation under grant 200020_137505.

This disclosure relates to cyclopropanation and to compounds for use therein.

Cyclopropanation, the conversion of a carbon-carbon double bond to a cyclopropane ring, is a chemical transformation used commonly in the synthesis of organic chemical compounds, in particular in the pharmaceutical, agrochemical, and flavors and fragrances industries. Cyclopropanation on a laboratory scale is commonly performed with the aid of diazo compounds, for example, diazomethane for methylenation reactions, and transition metal catalysts typically comprising copper or rhodium complexes. A wide variety of suitable catalysts is described in the review of Dzhemilev et at (*Russian Chemical Bulletin*, 1989, 38(8), 1707-1714).

On a larger, preparative scale relevant to production of commercially-significant quantities of cyclopropanated compounds, diazo compounds are avoided because of safety problems associated with their instability with respect to explosion, as well as the carcinogenicity of some of the best chemical precursors to diazo compounds.

One widely-exploited cyclopropanation reaction is the Simmons-Smith reaction (*J.Am.Chem.Soc.* 1958, 80, 5323, 1959, 81, 4256). This has the major advantage of being effective on a commercial scale, and it can deliver good-to-excellent yields. However, it produces more than stoichiometric amounts of zinc-containing waste, and furthermore typically requires diiodomethane, an expensive and potentially dangerous reagent.

It has now been found that it is possible to cyclopropanate carbon-carbon double bonds by a method that avoids the disadvantages of the prior art. There is therefore provided a method of preparing a cyclopropane ring-bearing compound of the formula I

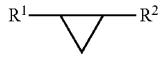
I in which $R^1$ and $R^2$ are independently selected from $C_1$-$C_{10}$ alkyl, optionally substituted, or $R^1$ and $R^2$, together with the bonds linking them to the cyclopropane ring, form a monocyclic or bicyclic ring system, which may comprise at least one hetero-atom, comprising the reaction of a compound of formula II $$R^1\text{—CH}=\text{CH—}R^2 \qquad \text{II}$$

in which $R^1$ and $R^2$ have the significances hereinabove defined, with a compound of formula III $$X\text{—CH}_2\text{—Y} \qquad \text{III}$$

in which X is selected a nucleofuge selected from halides and pseudohalides and Y is an electrofuge selected from boranes and borates, in the presence of a metal catalyst complex selected from those that are useful for catalytic cyclopropanation and those useful for catalyzing Heck coupling.

It is particularly unexpected that a compound of the formula III can perform this function under these conditions.

The moieties $R^1$ and $R^2$ in Formulae I and II may be selected from
(a) $C_1$-$C_{10}$ alkyl, optionally substituted;
(b) $R^1$ and $R^2$, together with the bonds linking them to the cyclopropane ring, form a monocyclic or bicyclic ring system, which may comprise at least one hetero-atom.

Particular examples of case (a) include 4-phenyl-1-butene, and styrene.

Particular example of case (b) include (left to right below) norbornene and cis cyclooctene:

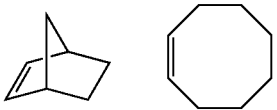 [SMILES: C1=CC2CCC1C2 ; C1=C\CCCCCC/1]

In the case of Formula III, the terms "nucleofuge" and "electrofuge" have their normal meanings, that is, respectively, a leaving group that retains the electron bonding pair from its previous bonding, and a leaving group that does not retain the bonding pair.

Typical examples of nucleofuge X include halogens and pseudohalogens (that is, compounds that are only partially halogen, or completely halogen-free). Examples of these include iodine and bromine. A particular example of a pseudohalogen includes acetate.

Typical examples of electrofuge Y include the trifluoroborate salts of alkali metals, such as sodium and potassium, and pinacol borane (4,4,5,5-tetramethyl-1,3,2-dioxaborolane).

The catalyst may be selected from any suitable catalyst known to be useful either for the cyclopropanation of olefins, or for use in the Heck reaction (see Zapf et al, *Topics in Catalysis*, 2002, 19, 101-109).

Particular examples are those complexes of metals of Group 10 (nickel, palladium, platinum) of the Periodic Table in the 0 or +2 oxidation state. A particular example is palladium.

A particular example of a catalyst is the Herrmann catalyst. This catalyst, trans-bis(acetato)bis[o-(di-o-tolylphosphino)benzyl]dipalladium(II), has the formula:

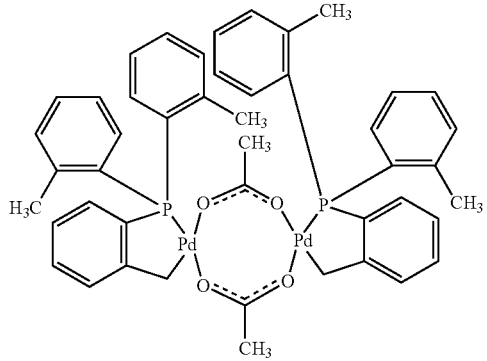

(see *Angew. Chem. Int. Ed. Engl.* 1995, 34, 1844-1848). and is readily commercially available.

A wide variety of conditions and reactants are possible. Typical solvents are dimethylformamide (DMF) and dimethylacetamide (DMA), optionally with added water and/or methanol. Tetrahydrofuran has also been found to work in some cases. In some cases, added bases, such as carbonate or fluoride salts, can be useful. However, the skilled person can, by simple, non-inventive experimentation, easily provide a suitable method with suitable conditions and reactants in every case.

The process provides a relatively easy method of cyclopropanating olefinic bonds. It is especially effective in cyclopropanating in-ring olefinic bonds, and this permits the ready synthesis of a considerable number of interesting compounds that previously could only be made with difficulty. Such compounds are useful as intermediates in other chemical processes, or as final products, and they are useful in a wide variety of chemical fields, such as pharmaceuticals, dyestuffs, flavours and fragrances.

This disclosure is further described with reference to the following non-limiting examples.

A number of preparations were made, and the results are shown in the following tables.

GENERAL PROCEDURE

In the glove box, a 5 mL Young Schlenk (approximately 10 mL total volume) was equipped with a glass coated stir bar. In the glove box, base (1.5 equiv), methylenation reagent (1.5 equiv), olefin (1 equiv), and catalyst (5 mol %) were transferred to the vial. A degassed solvent mixture of a polar solvent (16 mL/mmol substrate) and a ROH solvent (2 mL/mmol substrate) were added and the Schlenk was closed. After transferring the Schlenk outside the glove box, the reaction mixture was heated to 90° C. in an oil bath and stirred for 16 h. Then the reaction mixture was rapidly cooled to 0° C. in an ice bath. Consecutively undecane (0.4 equiv) as internal standard, $Et_2O$ (45 mL/mmol substrate) and water (45 mL/mmol substrate) were then added. The phases were separated and the aqueous phase was extracted with $Et_2O$ (45 mL/mmol substrate). The combined organic phases were washed with brine (45 mL/mmol substrate), dried over $MgSO_4$ and analyzed by GC-MS.

Procedure for Standard Reaction:

In the glove box, a 5 mL Young Schlenk (approximately 10 mL total volume) was equipped with a glass coated stir bar. In the glove box, $K_2CO_3$ (25.1 mg, 0.182 mmol), $KBF_3CH_2I$ (43.1 mg, 0.174 mmol), norbornene (11.0 mg, 0.117 mmol), and Hermann $Pd^{II}$-catalyst (2.74 mg, 0.00292 mmol, dimer so 5.0 mol % $Pd^{II}$) were transferred to the vial. A degassed solvent mixture of DMF (2 mL) and $H_2O$ (0.25 mL) were added and the Schlenk was closed. After transferring the Schlenk outside the glove box, the reaction mixture was heated to 90° C. in an oil bath and stirred for 16 h. Then the reaction mixture was rapidly cooled to 0° C. in an ice bath. Consecutively undecane (10 μL, 7.4 mg, 0.047 mmol) as internal standard, $Et_2O$ (5 mL/mmol substrate) and water (5 mL/mmol substrate) were then added. The phases were separated and the aqueous phase was extracted with $Et_2O$ (5 mL/mmol substrate). The combined organic phases were washed with brine (5 mL), dried over $MgSO_4$ and analyzed by GC-MS (method: 40° C. for 2 min, then from 40° C. to 300° C. in 17 min 20 sec [ramp: 15° C./min]). The tricyclo[3.2.1.0-2,4]octane was obtained in 98% yield according to GC-MS (standardized).

tricyclo[3.2.1.02,4]octane (compared to authentic sample, identical fragmentation pattern [GC-MS])—retention time: 5.81 min, area: 20343140, correction factor: 1.304/1.00 tricyclo[3.2.1.0-2,4]octane/undecane;

undecane—retention time: 8.65 min, area: 15889470.

The results are set forth in the following tables. Table 1 shows the screening of catalysts using norborene as the test olefin, and Table 2 shows the optimization of solvent, additives, and the electrofuge/nucleofuge combinations. Table 3 shows results for olefins other than norbornene.

TABLE 1

Screening of catalysts for the methylenation of norbornene.[a]

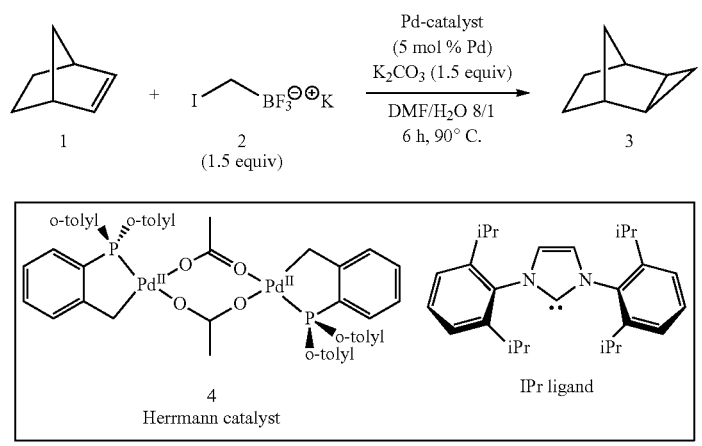

| entry | catalyst | yield | remaining 1[b] |
|---|---|---|---|
| 1 | none | 0% | 80% |
| 2 | $Pd^0(PPh_3)_4$ | 6% | 71% |
| 3[c] | $Pd^0(dba)_2$ + IPr | 2% | 81% |
| 4 | $Pd^0(IPr)_2$ | 37% | 45% |
| 5 | $Pd^0(P(tBu)_3)_2$ | 85% | 15% |
| 6 | $Pd^{II}$-Herrmann | 98% | 0% |
| 7 | $Pd^{II}IPrCl_2$-dimer | 88% | 4% |

[a]Conditions: scale 0.117 mmol 1, 0.06 M concentration of 1.
[b]Standardized GC-yield and recovery of 1.
[c]$Pd^0(dba)_2$ (5 mol %) and IPr ligand (6 mol %) were used.

TABLE 2

Optimization of norbornene methylenation using the Herrmann (4) and Pd⁰(P(tBu)₃)₂ (5) catalysts.[a]

[reaction scheme: norbornene 1 + XCH₂'B' (1.5 equiv) → 3, with 4 or 5 (5 mol % Pd), K₂CO₃ (1.5 equiv), DMF/H₂O, 6 h, 90° C.]

| # | cat | XCH$_2$'B' | base | DMF/H$_2$O | yield[b] | rem. 1[b] |
|---|---|---|---|---|---|---|
| 1 | 4 | ICH$_2$BF$_3$K (2) | K$_2$CO$_3$ | 8/1 | 98% | 0% |
| 2 | 5 | ICH$_2$BF$_3$K (2) | K$_2$CO$_3$ | 8/1 | 85% | 15% |
| 3 | 4 | ICH$_2$BF$_3$K (2) | K$_2$CO$_3$ | DMF only | 25% | 56% |
| 4 | 5 | ICH$_2$BF$_3$K (2) | K$_2$CO$_3$ | DMF only | 47% | 42% |
| 5 | 4 | ICH$_2$BF$_3$K (2) | none | 8/1 | 24% | 54% |
| 6 | 5 | ICH$_2$BF$_3$K (2) | none | 8/1 | 35% | 52% |
| 7 | 4 | ICH$_2$BF$_3$K (2) | none | DMF only | 1% | 73% |
| 8 | 5 | ICH$_2$BF$_3$K (2) | none | DMF only | 87% | 7% |
| 9[c] | 4 | ICH$_2$BF$_3$K (2) | K$_2$CO$_3$ | 8/1 | 38% | 37% |
| 10[c] | 5 | ICH$_2$BF$_3$K (2) | K$_2$CO$_3$ | 8/1 | 66% | 17% |
| 11 | 5 | BrCH$_2$BF$_3$K | none | DMF only | 7% | 73% |
| 12 | 5 | ICH$_2$B(OR)$_2$[d] | CsF[e] | DMF only | 70% | 16% |
| 13 | 5 | ICH$_2$B(OR)$_2$[d] | K$_2$CO$_3$ + CsF[e] | 8/1 | 92% | 8% |

[a]Conditions: scale 0.117 mmol 1, 0.06 M concentration of 1.
[b]Standardized GC-yield and recovery of 1.
[c]Before addition of 1 and the catalyst the B-reagent 2 was preactivated at 90° C. for 30 min.
[d]2-(iodomethyl)-4,4,5,5-tetramethyl-1,3,2-dioxaborolane was used.
[e]3.0 equiv of CsF was used.

TABLE 3

Methylenation of several electron-rich olefins using Herrmann catalyst 4.[a]

[reaction scheme: olefin 7 + ICH₂BF₃K (2) → cyclopropane 8 + β-H elim. product(s) 9, with 4 (5 mol % Pd), 10 (7.5%), 2 and K₂CO₃ (both 1.1 equiv), DMA/MeOH 8/1, 90° C., 24 h; 10 = P(otolyl)₃]

| # | substrate | cyclopropane[b] | β-H elimination product[b] | remaining 7[b] |
|---|---|---|---|---|
| 1 | 7a (cyclooctene) | 8a 31%[c] | 9a 7% | 58% |
| 2 | 7b (Ph-CH$_2$CH$_2$-CH=CH$_2$) | 8b 16%[b] | 9b 21% | 43% |
| 3 | 7c (Ph-CH=CH$_2$) | 8c 22%[c] | 9c 22%[c] | 39% |

[a]Conditions: scale 0.113-0.117 mmol, 0.06 M concentration of 7.
[b]Standardized GC-yield and recovery of 7.
[c]A mixture of several olefins was obtained.

The invention claimed is:

1. A method of preparing a cyclopropane ring-bearing compound of the formula I

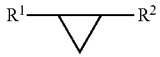   I in which $R^1$ and $R^2$ are independently selected from $C_1$-$C_{10}$ alkyl, optionally substituted, or $R^1$ and $R^2$, together with the bonds linking them to the cyclopropane ring, form a monocyclic or bicyclic ring system, which optionally comprises at least one hetero-atom, comprising the reaction of a compound of formula II $R^1$—CH═CH—$R^2$   II in which $R^1$ and $R^2$ have the significances hereinabove defined, with a compound of formula III

X—CH$_2$—Y   III in which X is a nucleofuge selected from halides and pseudohalides and Y is an electrofuge selected from boranes and borates, in the presence of a metal catalyst complex selected from those useful for catalytic cyclopropanation and those useful for catalyzing Heck coupling.

2. The method according to claim 1, in which the nucleofuge is selected from halogens and pseudohalogens.

3. The method according to claim 1, in which the electrofuge is selected from trifluoroborate salts of alkali metals, and pinacol borane.

4. The method according to claim 1 in which the catalyst is a Herrmann catalyst.

* * * * *